(12) United States Patent
Timbart et al.

(10) Patent No.: US 9,145,371 B2
(45) Date of Patent: Sep. 29, 2015

(54) PROCESS FOR THE PREPARATION OF (METH)ACRYLIC ESTERS AND DERIVATIVES

(71) Applicant: RHODIA OPERATIONS, Aubervilliers (FR)

(72) Inventors: Laurianne Timbart, Bensalem, PA (US); Nemesio Martinez-Castro, Bristol, PA (US); James Woods, Wilmington (DE); Howard Prokop, Feasterville, PA (US); Rastko Vukov, Princeton, NJ (US)

(73) Assignee: RHODA OPERATIONS, Paris (FR)

( * ) Notice: Subject to any disclaimer, the term of this patent is extended or adjusted under 35 U.S.C. 154(b) by 0 days.

(21) Appl. No.: 14/301,576

(22) Filed: Jun. 11, 2014

(65) Prior Publication Data

US 2014/0364619 A1  Dec. 11, 2014

Related U.S. Application Data

(60) Provisional application No. 61/833,661, filed on Jun. 11, 2013.

(51) Int. Cl.
*C07D 233/32* (2006.01)

(52) U.S. Cl.
CPC .................................. *C07D 233/32* (2013.01)

(58) Field of Classification Search
CPC .................................................... C07D 233/32
See application file for complete search history.

(56) References Cited

U.S. PATENT DOCUMENTS

| | | | | |
|---|---|---|---|---|
| 5,498,723 | A * | 3/1996 | Riondel et al. | 548/324.1 |
| 6,008,371 | A * | 12/1999 | Knebel et al. | 548/324.1 |
| 6,545,120 | B1 * | 4/2003 | Ooga et al. | 528/275 |
| 8,049,030 | B2 * | 11/2011 | Protzmann et al. | 560/217 |
| 8,916,724 | B2 * | 12/2014 | Knebel | 560/217 |

* cited by examiner

*Primary Examiner* — Joseph Kosack
*Assistant Examiner* — Amanda L Aguirre

(57) ABSTRACT

Transesterification processes for producing a compound of formula (I)

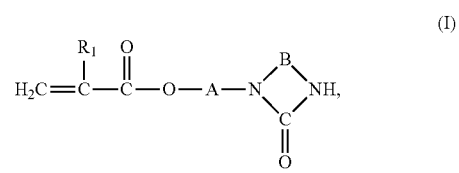

wherein R1 is H or a methyl group, A and B are each, independently, a linear or branched C2-C5 alkylene group, comprising reacting: an acrylate or methacrylate of formula (II)

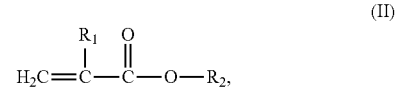

wherein R1 is H or a methyl group and R2 is a C1-C4 alkyl group, with a compound of formula (III)

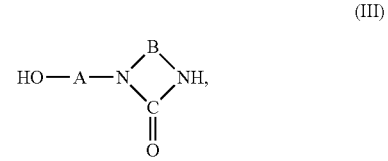

wherein the reaction is performed: (i) in the presence of calcium oxide and calcium hydroxide, and (ii) wherein the molar ratio of the compounds of formula (II) to formula (III) is less than 4:1 or 3:1 respectively.

5 Claims, No Drawings

PROCESS FOR THE PREPARATION OF (METH)ACRYLIC ESTERS AND DERIVATIVES

CROSS REFERENCE TO RELATED APPLICATIONS

This application claims the benefit of U.S. Provisional Patent Application No. 61/833,661 filed Jun. 11, 2013, incorporated herein by reference in its entirety.

FIELD OF THE INVENTION

The invention relates to a process of preparing esters of (meth)acrylic acid through transesterification, whereby the use of a particular transesterification catalyst mixture allows for less methyl methacrylate raw material to be used relative to other components.

BACKGROUND OF THE INVENTION

Methacrylic acid esters or acrylic acid esters are usually obtained by the reaction of alcohols with simple methacrylic acid esters such as methyl methacrylate or ethyl acrylate. Alkaline catalysts such as lithium hydroxides can be utilized in this transesterification processes. In addition, other metal catalysts such as titanium compounds may be used. Further, other transesterification catalysts that may be utilized include potassium cyanide, potassium cyanate and potassium thiocyanate.

SUMMARY OF THE INVENTION

In one aspect, described herein are transesterification processes for producing a compound of formula (I)

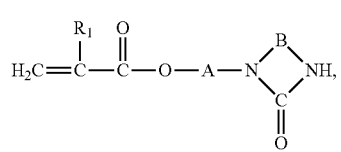

(I)

wherein R1 is H or a methyl group, A and B are each, independently, a linear or branched C2-C5 alkylene group, comprising reacting: an acrylate or methacrylate of formula (II)

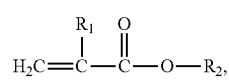

(II)

wherein R1 is H or a methyl group and R2 is a C1-C4 alkyl group, with a compound of formula (III)

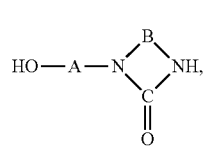

(III)

wherein the reaction is performed: (i) in the presence of calcium oxide and calcium hydroxide, and (ii) wherein the molar ratio of the compounds of formula (II) to formula (III) is less than 5:1, respectively.

In one embodiment, the molar ratio of the compounds of formula (II) to formula (III) is less than 4:1, respectively. In one embodiment, the molar ratio of the compounds of formula (II) to formula (III) is less than 3.5:1, respectively. In another embodiment, the molar ratio of the compounds of formula (II) to formula (III) is less than 3:1, respectively. In yet another embodiment, the molar ratio of the compounds of formula (II) to formula (III) is less than 2.5:1, respectively.

DETAILED DESCRIPTION

As used herein, the term "alkyl" means a saturated straight chain, branched chain, or cyclic hydrocarbon radical, including but not limited to, methyl, ethyl, n-propyl, iso-propyl, n-butyl, sec-butyl, t-butyl, pentyl, n-hexyl, and cyclohexyl.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkenyl, halo, haloalkyl, or amino, including but not limited to, phenoxy, phenyl, methylphenyl, dimethylphenyl, trimethylphenyl, chlorophenyl, trichloromethylphenyl, aminophenyl, and tristyrylphenyl.

As used herein, the term "alkylene" means a divalent saturated straight or branched chain hydrocarbon radical, such as for example, methylene, dimethylene, trimethylene.

As used herein, the terminology "$(C_r$-$C_s)$" in reference to an organic group, wherein r and s are each integers, indicates that the group may contain from r carbon atoms to s carbon atoms per group.

It has been surprisingly discovered that in the presence of a catalyst system of one or more alkaline earth metal salts, including alkaline earth metal oxides and alkaline earth metal hydroxides, heterocyclic or other compounds may be converted to corresponding acrylic or methacrylic acid esters with high purity by transesterification with acrylic or methacrylic acid esters. By utilizing the catalyst system as described herein, a lower amount of methyl methacrylate raw material relative to other raw material components (e.g., HEEA) is needed, which is desirable. In one embodiment, the heterocyclic compound is 1,2-hydroxyethyl-2-imidazolinone (HEEA).

The alkaline earth metal salt may be an alkaline earth metal oxide and/or an alkaline earth metal hydroxide. In one embodiment, the alkaline earth metal salt may be an alkaline earth metal oxide such as magnesium oxide, calcium oxide or barium oxide. In another embodiment, the alkaline earth metal salt may be an alkaline earth metal hydroxide such as lithium hydroxide or calcium hydroxide. In one particular embodiment, the catalyst system comprises at least one alkaline earth metal oxide and at least one an alkaline earth metal hydroxide. In another embodiment, the catalyst system comprises one alkaline earth metal oxide and one an alkaline earth metal hydroxide. In specific embodiment, the catalyst system comprises calcium oxide and calcium hydroxide.

If the catalyst system is a mixture of an and alkaline earth metal oxide and an alkaline earth metal hydroxide, the weight ratio of alkali earth metal oxide to alkaline earth metal hydroxide can be 5:1 to 1:5. It is understood that the weight ratio includes any range or ratio in-between 5:1 to 1:5. For example, the weight ratio would include, but is not limited to 4.5:1, 4:1, 3:1, 2:1, 1:1, 1.5:1, 1:2, 1:3, 1:4 and 1:4.2, among others.

To produce compounds of formula (I), an acrylate or methacrylate of the formula (II) is utilized, wherein R2 is an alkyl group having 1 to 4 carbon atoms. Compounds of formula (II) include, for example, methyl methacrylate, ethyl methacrylate, propyl acrylate, n-butyl acrylate, i-propyl methacrylate, i-butyl methacrylate, and n-butyl methacrylate. In one particular embodiment, the compound of formula (II) is methyl methacrylate or ethyl methacrylate. In another embodiment, the compound of formula (II) is methyl methacrylate. Formula (III) includes compounds where either or both of A or B are branched or unbranched C2-C5 alkylene groups, such as, for example: —(CH2)2—, —(CH2)3—, —(CH2)4—, —CH2CH(CH3)CH2—, and —CH2C(CH3)2CH2—. The heterocyclic compound, in one embodiment, contains 5 carbon atoms. The heterocyclic compound, in another embodiment, contains 6 carbon atoms. In one embodiment, formula (III) is 1,2-hydroxyethyl-2-imidazolinone.

Generally, the polymerization inhibitors are utilized during the process to avoid side products produced by polymerization. Polymerization inhibitors such as phenothiazine, hydroquinone monomethyl ether, and oxygen can be utilized in the process.

The transesterification process is typically performed at a temperature of between 30 and 180° C., typically between 50 and 130° C., more typically, between 50 and 90° C., in the presence of 0.01 to 10 wt % catalyst system by weight of the reaction mixture.

Equimolar amounts of reactants of formula (II) and formula (III) are reacted to form the desired end product, i.e., a compound of formula (I). It is desirable to form the end-product of formula (I) at high conversion rate, generally above 80% conversion. In one embodiment, it is desirable to have a conversion rate of at least 70%, or in other embodiments a conversion rate of at least 75%, or in other embodiments a conversion rate of at least 77% or 79%, or in other embodiments a conversion rate of at least 82%.

Typically, one would use an excess of starting compound according to formula (II) during the conversion, relative to the compound of formula (III). However, excessive amounts of compounds of formula (II) relative to formula (III) are not desirable due to increased cost and waste. Typically, however, lower than a 5:1 weight ratio of formula (II) to formula (III), respectively, results in a lower conversion rate, which is also undesirable.

It has been surprisingly discovered that through utilizing the catalyst systems as described herein, weight ratios lower than 5:1 of formula (II) to formula (III), respectively, can be achieved at high conversion rates, typically greater than 70% conversion, more typically greater than 75% conversion, even more typically greater than 80% conversion. It also has been surprisingly discovered that use of the catalyst systems as described herein allow for the end formulation/mixture to be colorless, which is desirable in that it gives flexibility to end-formulators. The use of other catalyst systems gives off a color, e.g., yellowish color, which is undesirable.

Experiments

Example 1

1,2-hydroxyethyl-2-imidazolinone (HEEU) was placed in a 250 mL round-bottom flask equipped with a column and reflux condenser. The HEEU was dried under full vacuum. The obtained material, which is a waxy-solid at room temperature, was melted under a NOx flow. Polymerization inhibitors of methoxyphenol (MEHQ) and phenothiazine (PTZ) were charged to the reactor. The catalyst system of 300 ppm of calcium oxide (CaO) and 250 ppm of calcium hydroxide (Ca(OH)2) was charged to the reactor as a slurry in methyl methacrylate (MMA). MMA was charged in the reactor up to a molar ratio of 3:1 (MMA:HEEU), as compare to the initial HEEU. The reactor was held during the required time for 3 to 5 hours at a temperature between 50 and 90° C., to distill of the MMA-methanol azeotrope and drive the reaction to completion, after which time the reactor was cooled. The solution was filtered to remove the catalysts by using a filter aid. Depending on the final product specifications: excess MMA was stripped out by applying full vacuum during the required time or MMA was added to the system and the solution is mixed for homogenization.

Example 2

Comparative examples utilizing typical catalysts were prepared against the catalyst systems as descried herein. Comparative examples as shown in Table 1 are as follows: R-1094-135-28, R-1094-116-28 and R-1094-133-28, which utilize LiOH and CaO as the catalyst system.

TABLE 1

| | Inhibitor PTZ (ppm) | Inhibitor MEHQ (ppm) | Catalyst CaO (ppm) | Catalyst Ca(OH)2 (ppm) | MMA/OH | Holding time (h) | CC/min Nox | Conversion molar % (HPLC) |
|---|---|---|---|---|---|---|---|---|
| R-1075-77-00 | 100 | 400 | 300 | 250 | 5 to 1 | 4 | 60 | 88.94 |
| R-1094-135-28 | 100 | 400 | 300 | 250 LiOH | 5 to 1 | 4 | 60 | 79.05 |
| R-1094-116-28 | 100 | 400 | 724 | 277 LiOH | 5 to 1 | 4 | 60 | 87.64 |
| R-1094-58-28 | 100 | 400 | 300 | 250 | 3 to 1 | 4 | 60 | 84.27 |

TABLE 1-continued

| | Inhibitor PTZ (ppm) | Inhibitor MEHQ (ppm) | Catalyst CaO (ppm) | Catalyst Ca(OH)2 (ppm) | MMA/OH | Holding time (h) | CC/min Nox | Conversion molar % (HPLC) |
|---|---|---|---|---|---|---|---|---|
| R-1094-133-28 | 100 | 400 | 300 | 250 LiOH | 3 to 1 | 4 | 60 | 65.91 |

As can be seen from Table 1, the comparative examples have a high conversion of final product (i.e., compound of formula (I)) when the molar ratio is high at 5:1 of MAA: HEEU, respectively (87%, 79% conversion). The comparative examples utilize 277 ppm LiOH, 724 ppm CaO. The catalyst system of the present invention (250 ppm LiOH, 300 ppm CaO) had a higher conversion at the same 5:1 weight ratio of MAA:HEEU, respectively (89% conversion).

However, when using a ratio 3:1 of MAA:HEEU, respectively, the conversion of final product (i.e., compound of formula (I)) of the comparative example is at a low 66% conversion. The catalyst system of the present invention (250 ppm LiOH, 300 ppm CaO) had a much higher conversion at the same 3:1 weight ratio of MAA:HEEU, respectively (85% conversion), versus a 66% conversion rate of the comparative example.

The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation in scope is to be inferred.

What is claimed is:

1. A process for producing a compound of formula (I)

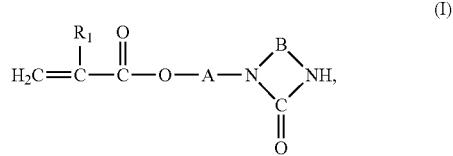

wherein R1 is H or a methyl group, A and B are each, independently, a linear or branched C2-C5 alkylene group, comprising reacting:

an acrylate or methacrylate of formula (II)

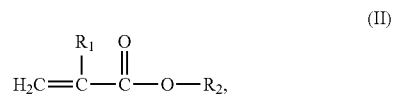

wherein R1 is H or a methyl group and R2 is a C1-C4 alkyl group, with a compound of formula (III)

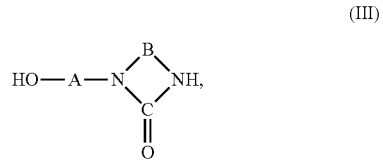

wherein the reaction is performed:
   (i) in the presence of calcium oxide and calcium hydroxide, and
   (ii) wherein the molar ratio of the compounds of formula (II) to formula (III) is less than 5:1, respectively.

2. The process of claim 1 wherein the molar ratio of the compounds of formula (II) to formula (III) is less than 4:1, respectively.

3. The process of claim 1 wherein the molar ratio of the compounds of formula (II) to formula (III) is less than 3.5:1, respectively.

4. The process of claim 1 wherein the molar ratio of the compounds of formula (II) to formula (III) is less than 3:1, respectively.

5. The process of claim 1 wherein the molar ratio of the compounds of formula (II) to formula (III) is less than 2.5:1, respectively.

* * * * *